United States Patent
Pállinger et al.

(10) Patent No.: US 11,168,368 B2
(45) Date of Patent: Nov. 9, 2021

(54) NON-INVASIVE METHOD TO ASSESS EMBRYO COMPETENCE

(71) Applicants: SEMMELWEIS EGYETEM, Budapest (HU); PÉCSI TUDOMÁNYEGYETEM, Pécs (HU)

(72) Inventors: Éva Pállinger, Budapest (HU); Júlia Szekeres, Pécs (HU); Zoltán Bognár, Pécs (HU); Krisztina Gödöny, Pécs (HU); József Bódis, Pécs (HU); Edit Buzás, Budapest (HU)

(73) Assignees: Pécsi Tudományegyetem, Pécs (HU); Semmelweis Egyetem, Budapest (HU)

( * ) Notice: Subject to any disclaimer, the term of this patent is extended or adjusted under 35 U.S.C. 154(b) by 657 days.

(21) Appl. No.: 15/779,136

(22) PCT Filed: Nov. 25, 2016

(86) PCT No.: PCT/HU2016/050058
§ 371 (c)(1),
(2) Date: May 25, 2018

(87) PCT Pub. No.: WO2017/089850
PCT Pub. Date: Jun. 1, 2017

(65) Prior Publication Data
US 2018/0274030 A1 Sep. 27, 2018

(30) Foreign Application Priority Data
Nov. 27, 2015 (HU) .................. P1500579

(51) Int. Cl.
| | | |
|---|---|---|
| C12Q 1/68 | (2018.01) | |
| C12Q 1/6881 | (2018.01) | |
| C12Q 1/6841 | (2018.01) | |
| C12Q 1/6883 | (2018.01) | |
| G01N 15/14 | (2006.01) | |

(52) U.S. Cl.
CPC ......... *C12Q 1/6881* (2013.01); *C12Q 1/6841* (2013.01); *C12Q 1/6883* (2013.01); *G01N 15/14* (2013.01); *G01N 2015/1486* (2013.01)

(58) Field of Classification Search
None
See application file for complete search history.

(56) References Cited

U.S. PATENT DOCUMENTS
2016/0138104 A1  5/2016  Hamamah et al.

OTHER PUBLICATIONS

Rosenbluth et al., Human embryos secrete microRNAs into culture media—a potential biomarker for implantation. Fertil Steril; 2014; 101:1493-1500. (Year: 2014).*

Ferreira et al., Human embryos release extracellular vesicles which may act as indicators of embryo quality. Pesentation O-253; session 66: Embryo quality: does it predict pregnancy? Human Reproduction; 2013; vol. 28, Issue suppl_1, Jun. 2013, pp. i104-i106. Published: Jul. 10, 2013. (Year: 2013).*
Pospichalova et al., Simplified protocol for flow cytometry analysis of fluorescently labeled exosomes and microvesicles using dedicated flow cytometer. Journal of Extracellular Vesicles; Mar. 2015; 1-15. (Year: 2015).*
Nolan JP., Flow Cytometry of Extracellular Vesicles: Potential, Pitfalls, and Prospects. Current Protocols in Cytometry; Jul. 2015; p. 13.14.1-13.14.16; (Year: 2015).*
Ferreira et al., Human embryos release extracellular vesicles which may act as indicators of embryo quality. Presentation O-253; session 66: Embryo quality: does it predict pregnancy? Human Reproduction; 2013; vol. 28, Issue suppl_1, Jun. 2013, pp. i104-1106. Published: Jul. 10, 2013. (Year: 2013).*
Stigliani et al., Mitochondrial DNA in Day 3 embryo culture medium is a novel, non-invasive biomarker of blastocyst potential and implantation outcome. Molecular Human Reproduction; 2014; vol. 20; No. 12: 1238-1246. (Year: 2014).*
Stigliani et al., Mitochondrial DNA content in embryo culture medium is significantly associated with human embryo fragmentation. Human Reproduction; 2013; vol. 28; No. 10: 2652-2660. (Year: 2013).*
Zaborowski et al., Extracellular Vesicles: Composition, Biological Relevance, and Methods of Study. BioScience 65; Aug. 2015; vol. 65; No. 8: 783-797. (Year: 2015).*
Waldenstrom et al., Cardiomyocyte Microvesicles Contain DNA/RNA and Convey Biological Messages to Target CellsPLOS One; 2012; 7;4;e34653: p. 1-7. (Year: 2012).*
PI Protocol. Propidium Iodide Nucleic Acid Stain Product Information, Molecular Probes;1999: p. 1-3. (Year: 1999).*
Wu et al., Exosomes: Improved methods to characterize their morphology, RNA content, and surface protein biomarkers. Analyst; Oct. 7, 2015; 140(19): 6631-6642. (Year: 2015).*
Stigliani et al.: "Mitochondrial DNA content in embryo culture medium is significantly associated with human embryo fragmentation", Human Reproduction, 28 (10) 2652-2660, 2013.
Ferreira et al.: "Human embryos release extracellular vesicles which may act as indicators of embryo quality", Human Reproduction 28 (Supp 1) Abstract, 2013.
Stigliani et al.: "Mitochondrial DNA in Day 3 embryo culture medium is a novel, non-invasive biomarker of blastocyst potential and implantation outcome", Molecular Human Reproduction 20 (12) 1238-1246, 2014.
Tannetta et al.: "Extracellular vesicles and reproduction—promotion of successful pregnancy", Cellular & Molecular Immunology (2014) 11, 548-563.

* cited by examiner

*Primary Examiner* — Juliet C Switzer
*Assistant Examiner* — Wahwah T Johnson
(74) *Attorney, Agent, or Firm* — Jason D. Voight

(57) ABSTRACT

The invention relates to a non-invasive, simple, inexpensive, quick method to assess embryo competence in vitro by detecting nucleic acid-containing extracellular vesicles in the culture medium of the embryo. The culture medium may be fixed before being stained with propidium iodide and analysed by flow cytometry.

11 Claims, 12 Drawing Sheets

NON-INVASIVE METHOD TO ASSESS EMBRYO COMPETENCE

Figure 1:
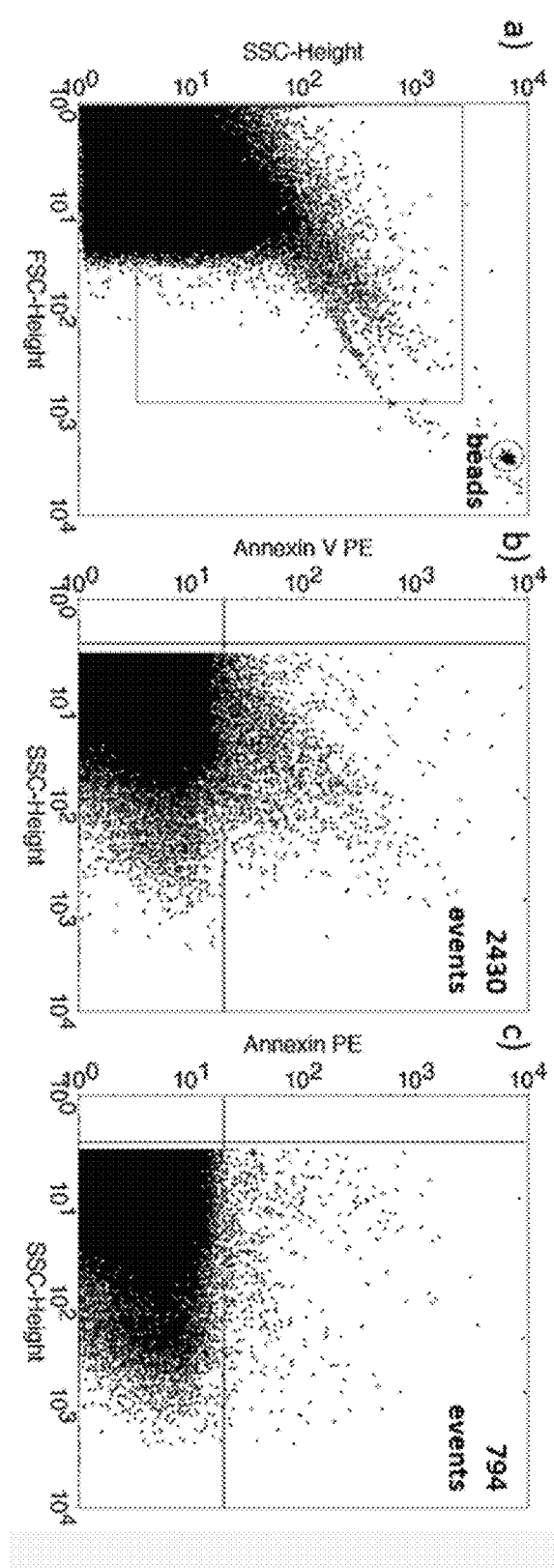

This is the national stage of International Application PCT/HU2016/050058, filed 25 Nov. 2016.

FIELD OF THE INVENTION

The invention relates to a non-invasive, simple, inexpensive, quick method to assess embryo competence in vitro by detecting nucleic acid-containing extracellular vesicles in the culture medium of the embryo.

BACKGROUND OF THE INVENTION

The efficiency of embryo implantation is surprisingly low in humans. This can either be attributed to the high rate of chromosomally abnormal embryos, or to uterine factors, if the embryo is chromosomally normal. Ideally, a competent embryo should have good chances to implant into a receptive endometrium. However, successful outcome is also related to the age of the mother. The percentage of aneuploid embryos increases with maternal age, reaching 80% over the age of 40[1-4], and many of these chromosomally abnormal embryos fail to implant[5-9], which explains that according to a rather conservative estimate only 50% of human conceptions will result in pregnancy[10].

In an attempt to increase the chances of pregnancy in infertile women, many in vitro fertilization (IVF) centres transfer more than one embryos. This in turn also increases the hazard of twin pregnancies. Multiple pregnancies are among the most common causes of preterm birth, along with the increased risk for prematurity. Therefore, it would be of importance to select the embryo that is most likely to implant and to transfer that particular embryo only.

Enormous efforts have been devoted to finding the appropriate method to identify the competent embryo. Selection, based on the morphological features of the embryo is highly prone to subjectivity. Morphokinetic measurements provide more objective data. By using time-lapse imaging, the development of the embryo can be observed in a closed system, and thus, in contrast to morphological evaluation, in this case the culture conditions are stable. Some studies reported an elevated pregnancy rate when morphokinetic parameters were used for embryo selection, however, large randomized trials are still missing.

In spite of its invasive nature, pre-implantation genetic screening for aneuploidy seemed very promising. However, recent randomised trials did not confirm the favourable effects, as suggested by the initial (non-randomised) studies. This can be partly explained by the invasiveness of the method itself, and the inherent problems in testing embryos at different stages of development.

The ideal test should be non-invasive, simple and quick, so that it could be performed immediately before fresh transfer. This would imply detection of changes in the spent embryo culture medium that would reflect the functional state and vitality of the embryo. Unfortunately, tests detecting the glucose or amino acid metabolism or oxygen consumption of the embryo require sophisticated equipment. Therefore, they are not suitable for high throughput routine screening.

Extracellular vesicles (EVs) are phospholipid bilayer enclosed particles which are constitutively produced by both eukaryotic and prokaryotic cells. Among EVs exosomes are the smallest particles, with a diameter of 100 nm or less. Extracellular vesicles range from 100 to 800 nm and apoptotic bodies are larger than 1000 nm. On the basis of their specific exofacial and intravesicular molecular pattern (DNA, RNA, protein), EVs play important role in intercellular communication, both in physiological and pathological processes. EVs are detectable in body fluids including peripheral blood, urine, cerebrospinal fluid, synovial fluid, or amniotic fluid. Although all cell types can produce any subpopulations of EVs, the different vesicles are induced by various stimuli[11,12].

The role of extracellular vesicles has been shown in several reproductive processes. During the early stages of the human reproductive process, the ovarian follicle, seminal fluid, endometrium, embryo and trophoblast cells are all possible sources of EVs that have the potential to modulate maternal immune function locally. EV signalling may be through protein or lipid ligand-receptor interactions or micro-interfering RNAs (miRNAs) which have been found in both soluble and EV associated forms in various bodily fluids[13].

Several studies have shown that both mitochondrial DNA (mtDNA) and chromosomal DNA were found in EVs[14]. Kropp et al. showed the presence of miRNAs in in vitro human and bovine culture media. They suggested that embryo quality or developmental competence correlated with miRNA expression. They also found however that the expression of the miRNA did not correlate to the degree of gene expression observed within the embryo[15]. WO 2014202696 A1 describes a method for determining the quality of an embryo by determining the level of the cell free nucleic acids and/or determining the presence and/or expression level of at least one specific nucleic acid sequence in the nucleic acid extraction. Extracellular vesicles are not mentioned.

Tannetta et al. suggested that preimplantation embryos might produce extracellular vesicles, however they point out that in vitro fertilization (IVF) culture media alone contains high levels of EVs, possibly from the nutrients supplemented for embryo growth, making detection of specific embryo derived EVs challenging[13].

Some data suggest that the concentrations of placental-derived exosomes in the maternal blood could be a potential marker of abnormal placentation[16,17].

Different methods are used for the assessment of the size, morphology, molecular pattern, and cellular origin of EVs. The most often used techniques are Western blotting, nanoparticle tracking analysis (NTA), tunable resistive pulse sensing (TRPS), electron microscopy (EM), cryo-EM and flow cytometry. Flow cytometry is the most widely used method to investigate EVs Is, however, as flow cytometers are typically designed to examine cells, analysing small EVs is associated with a number of limitations. Conventional flow cytometry can only be used to phenotype EVs down to approximately 300 nm in size, and the "noise" generated by cells, debris and protein aggregates needs to be gated out.

In view of the above deficiencies of the prior art an improved non-invasive, in vitro method suitable to assess embryo competence and to select embryos having limited probability for resulting in a successful pregnancy is highly needed.

Definitions

The term "clinical pregnancy" as used herein relates to a state of pregnancy wherein the fetus can be detected using ultrasonography. Clinical pregnancy may be confirmed four weeks after embryo transfer. Clinical pregnancy may be defined by the presence of foetal heartbeat, and implantation failure by the lack of the former, together with the lack of beta hCG on week 2 after the transfer.

"Nucleic acid stain" (or nucleic acid dye) refers to a stain suitable for staining nucleic acid, while the term "DNA stain" (or DNA dye) refers to a stain suitable for staining DNA.

SHORT DESCRIPTION OF THE INVENTION

An in vitro method for non-invasive embryo competence assessment is provided, the method comprising the following steps:
a) determining the number of nucleic acid-containing extracellular vesicles (EV) in samples of a plurality of media of the same type, which were used to culture the embryos,
b) identifying an embryo with a higher number of nucleic acid-containing EVs in its culture medium as having a limited probability for clinical pregnancy, relative to an embryo with a lower number of nucleic acid containing EVs in its culture medium.

Reliability of known competence assessment methods of cultured embryos is generally low, therefore the improvement of non-invasive competence assessment is highly desirable. Ferreira et al. studied the size distribution of EVs in culture media of embryos and hypothesized that EV size might have the potential to predict embryo quality[19]. The quality of the embryos has been determined by its morphologic parameters, not confirmed by implantation or (clinical) pregnancy. Further, Ferreira et al. only examined samples from culture media previously containing an embryo. Control samples (i.e. samples from the same type of culture medium but not containing an embryo) were not assessed. Embryo culture media are well known to contain EVs[13], this fact has been also confirmed by the studies reported herein. Ferreira et al. recognized the presence of DNA in EVs, but did not consider it relevant. On the contrary, correlation between CellMask-stained EVs (that is, all EVs) and embryo quality has been suggested. None of the prior art documents—including the study of Ferreira et al. and Tannetta et al.—have realized or suggested that EVs in the culture medium of an embryo may be differentiated based on their DNA content and that the number of DNA-containing EVs may be indicative of embryo competence, instead of the total number of EVs.

The term "culture media" refers to any kind of culture media suitable to culture human embryos. In the method according to the invention, samples of the same type of culture medium are compared. The culture medium used for human embryos preferably does not comprise nucleic acid-containing EVs or preferably does not comprise DNA-containing EVs before the initiation of culturing (i.e. before the fertilized oocyte is placed in the culturing vessel containing the culture medium).

The in vitro method for non-invasive embryo competence assessment, wherein step a) comprises fixing the sample of the embryo culture medium prior to staining by a fluorescent nucleic acid stain suitable for use in fluorescence activated cell sorting (FACS, flow cytometry).

The in vitro method for non-invasive embryo competence assessment, wherein step a) comprises the analysis of EVs by FACS (flow cytometry).

1. In a preferred embodiment step a) comprises
   fixing the sample,
   staining the EVs in the sample by a fluorescent nucleic acid stain suitable for use in flow cytometry,
   analysing the EVs stained by the nucleic acid stain using flow cytometry.

In a preferred embodiment the embryos are developed from oocytes derived from the same female. The embryos which are developing from oocytes derived from the same female are cultured individually. In this particular embodiment the method comprises the following steps:
a) determining the number of nucleic acid-containing extracellular vesicles (EV) in samples of a plurality of media which were used to culture the embryos developing from oocytes derived from the same female,
b) identifying an embryo with a higher number of nucleic acid-containing EVs in its culture medium as having a limited probability for clinical pregnancy, relative to an embryo with a lower number of nucleic acid-containing EVs in its culture medium.

In the embodiment when the oocytes are derived from the same female, step a) may comprise the following:
fixing the sample,
staining the EVs in the sample by a nucleic acid fluorescent stain suitable for use in flow cytometry,
analysing the EVs stained by the nucleic acid stain using flow cytometry.

For fixing the sample commercially available buffer solutions suitable for fixing cell membrane may be used. Formaldehyde, glutaraldehyde, and paraformaldehyde are examples of generally used fixing solutions.

For staining any stain (dye) that is suitable for flow cytometry and binds nucleic acids may be used. Dyes suitable for use in the method of the invention are e.g. propidium iodid (PI), ethidium bromide, and cyanine dyes, such as SYBR Gold, SYBR Green I and SYBR Green II, EvaGreen, YO-PRO, YOYO and the like. DNA binding stains are preferred. Nucleic acid stains having a greater affinity to DNA than to RNA are preferred.

In a preferred embodiment the method according to the invention comprises the following steps:
providing samples of a plurality of media which were used to culture the embryos,
fixing the samples with an agent suitable for fixing cell membranes, preferably formaldehyde, glutaraldehyde or paraformaldehyde,
staining the samples with a nucleic acid-labelling fluorescent stain, preferably propidium iodide or a cyanine dye,
analysing the stained EVs by flow cytometry, and
identifying an embryo with a higher number of nucleic acid-containing EVs in its culture medium as having a limited probability for clinical pregnancy, relative to an embryo with a lower number of nucleic acid-containing EVs in its culture medium.

In an embodiment when the oocytes are derived from the same female, step a) may comprise the following:
providing samples of a plurality of media which were used to culture the embryos developing from oocytes derived from the same female,
fixing the samples with an agent suitable for fixing cell membranes, preferably formaldehyde, glutaraldehyde or paraformaldehyde,
staining the samples with a nucleic acid-labelling fluorescent dye, preferably propidium iodide or a cyanine dye,
analysing the stained EVs by flow cytometry, and
identifying an embryo with a higher number of nucleic acid-containing EVs in its culture medium as having a limited probability for clinical pregnancy, relative to an embryo with a lower number of nucleic acid-containing EVs in its culture medium.

The method for non-invasive embryo competence assessment may be performed from day 3 after oocyte fertilization, e.g. on day 3 or day 5 of culturing.

The method for non-invasive embryo competence assessment is preferably performed on day 5 after oocyte fertilization.

In preferred embodiments of the method according to the invention the nucleic acid is DNA.

A method for determining a cut-off value for identifying embryos having limited competence is also provided.

A method for determining a cut off level for identifying embryos with limited competence comprises the following steps:
- determining the number of nucleic acid-containing extracellular vesicles in samples of a plurality of culture medium of the same type which were used to culture the embryos,
- relating the number of nucleic acid-containing extracellular vesicles in said samples to the outcome of the transfer,
- determining the number of nucleic acid-containing extracellular vesicles that distinguishes the culture media from embryos with a positive outcome from the culture media from embryos with a negative outcome.

The positive outcome may be implantation, clinical pregnancy, birth. Negative outcome may be e.g. implantation failure, lack of clinical pregnancy. In a preferred embodiment the number of nucleic acid-containing extracellular vesicles is determined by the method defined in the numbered (1) paragraph hereinabove. In preferred embodiments the nucleic acid is DNA.

SHORT DESCRIPTION OF THE DRAWINGS

Figure 2:
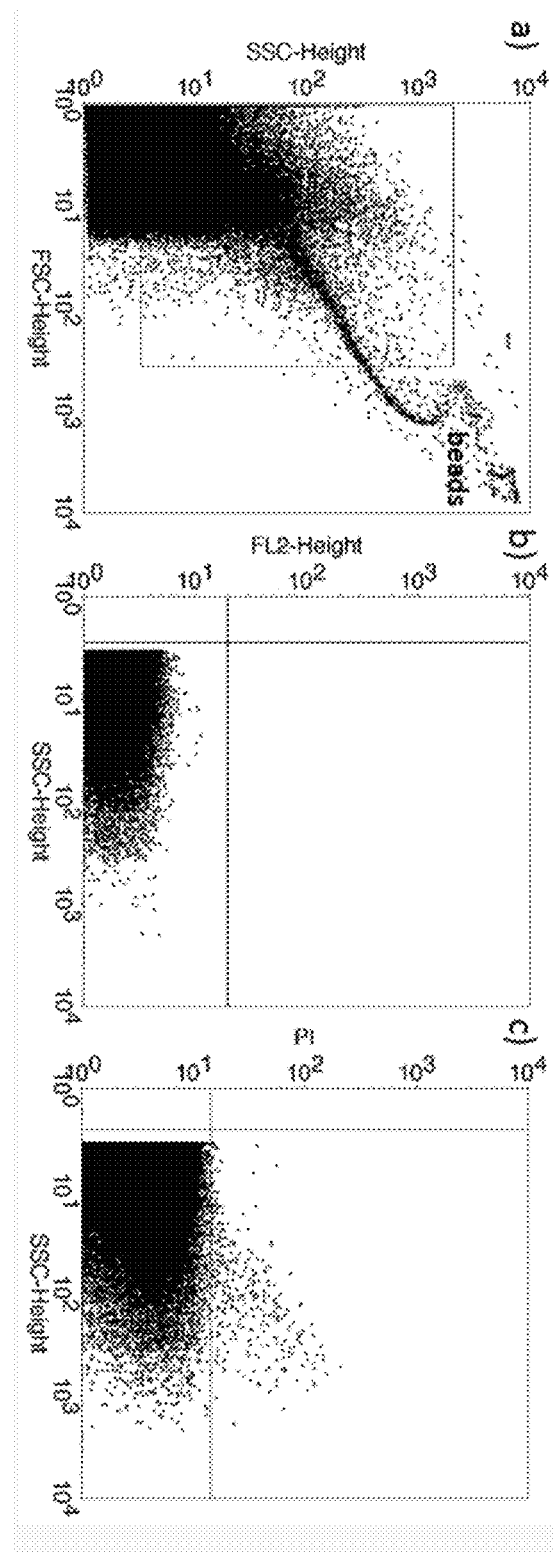

FIG. 1 Annexin V staining of embryo-derived EVs in embryo culture medium
a) Representative FSC-SSC dot plot shows the size distribution of EVs in embryo culture medium
b) Representative dot plot shows the phycoerythrin (PE) fluorescence of EVs after AnnexinV-PE labelling
c) Representative dot plot shows the PE fluoresce after Triton-X 100 differential detergent lysis FIG. 2 Propidium iodide (PI) staining of embryo-derived EVs in embryo culture medium
a) Representative FSC-SSC dot plot shows the size distribution of EVs in embryo culture medium
b) Representative dot plot shows the autofluorescence of embryo culture medium in FL2 channel (embryo culture medium+4% formaldehyde solution+PI, without EVs.
c) Representative dot plot shows the PI fluorescence of 4% formaldehyde fixed embryo-derived EVs in embryo culture medium.

Figure 3:
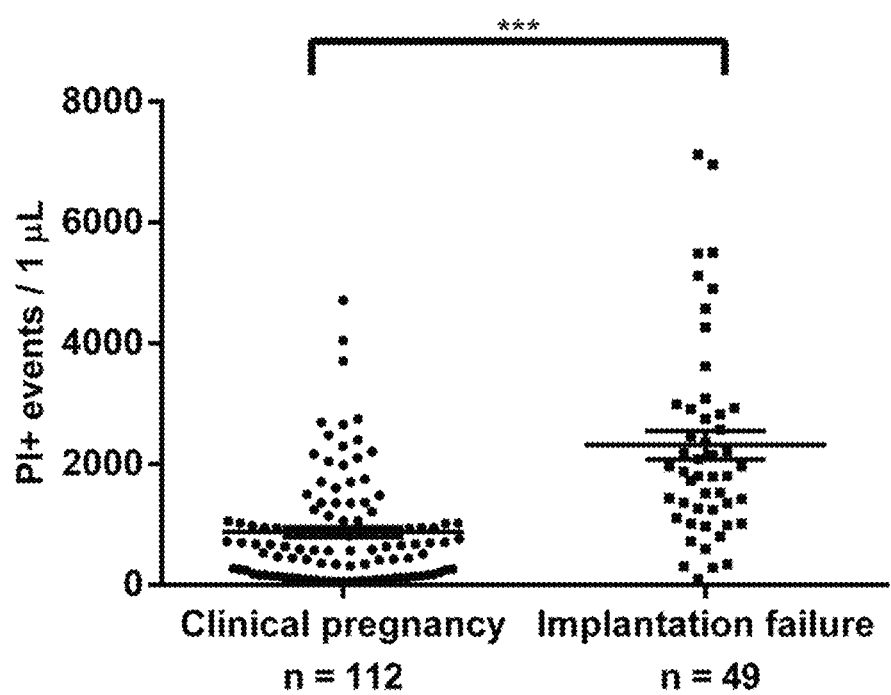

FIG. 3 Propidium iodide (PI)+EVs in culture medium of embryos resulting in clinical pregnancy or implantation failure ***P<0.001

Figure 4:
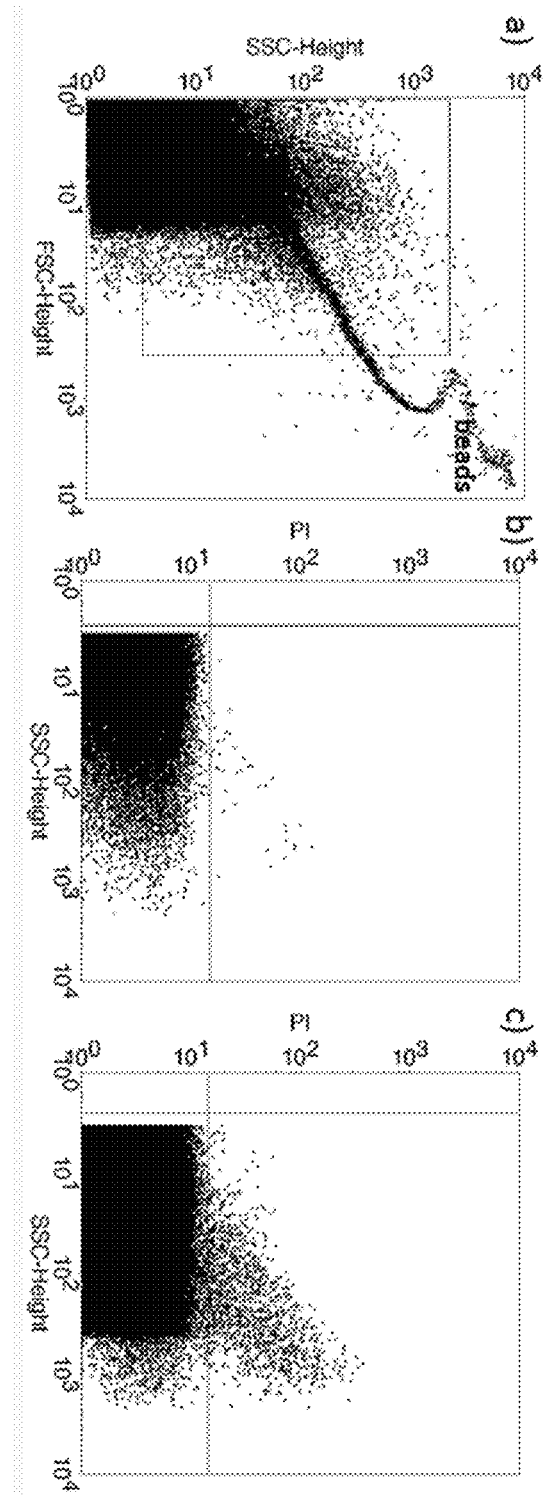

FIG. 4 Propidium iodide (PI) staining of embryo-derived EVs in embryo culture medium. Two transferred embryos resulting in singleton pregnancy
a) Representative FSC-SSC dot plot shows the size distribution of EVs in embryo culture medium
b) and c) dot plots show the PI fluorescence of EVs transferred to the same mother.

Figure 5:
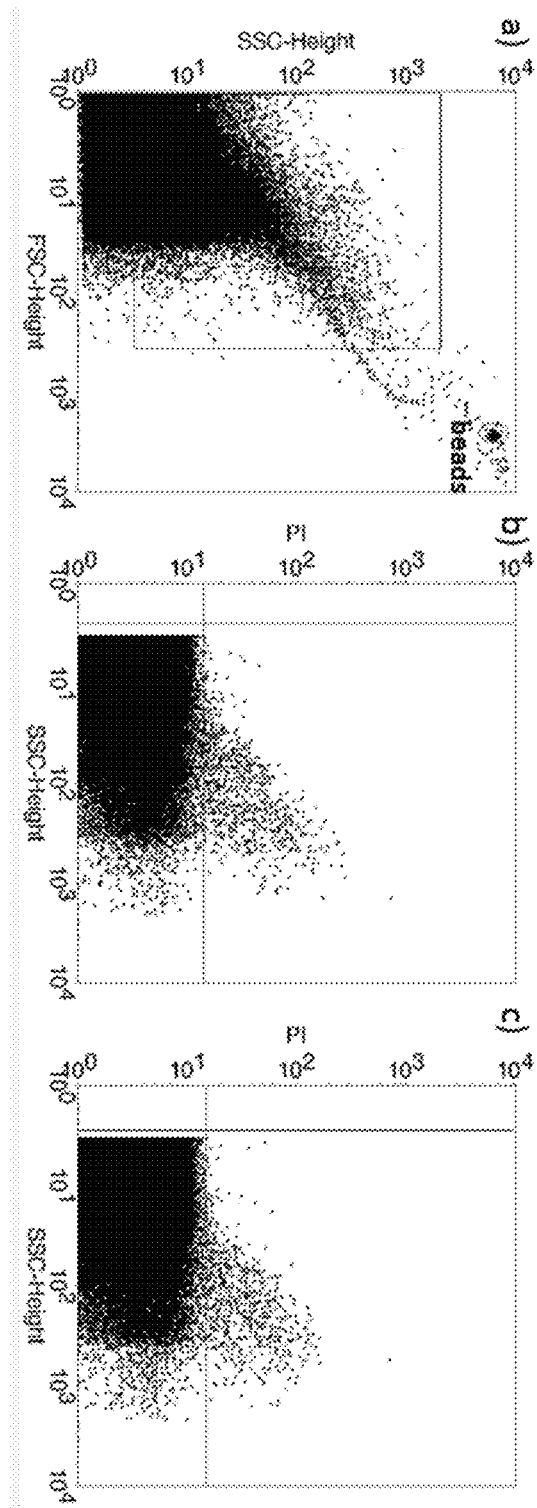

FIG. 5 Propidium iodide (PI) staining of embryo-derived EVs in embryo culture medium. Two transferred embryos resulting in pregnancy failure
a) Representative FSC-SSC dot plot shows the size distribution of EVs in embryo culture medium
b) and c) dot plots show the PI fluorescence of EVs transferred to the same mother.

Figure 6:
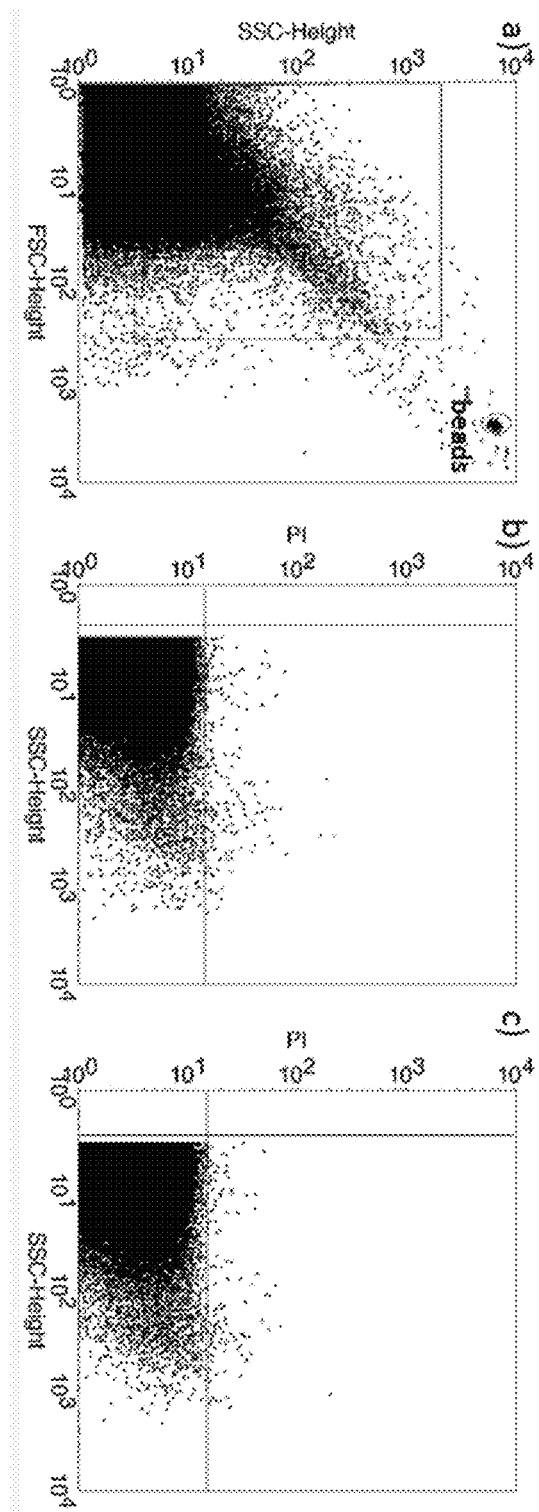

FIG. 6 Propidium iodide (PI) staining of embryo-derived EVs in embryo culture medium. Two transferred embryos, resulting in twin pregnancy
a) Representative FSC-SSC dot plot shows the size distribution of EVs in embryo culture medium
b) and c) dot plots show the PI fluorescence of EVs transferred to the same mother.

Figure 7:
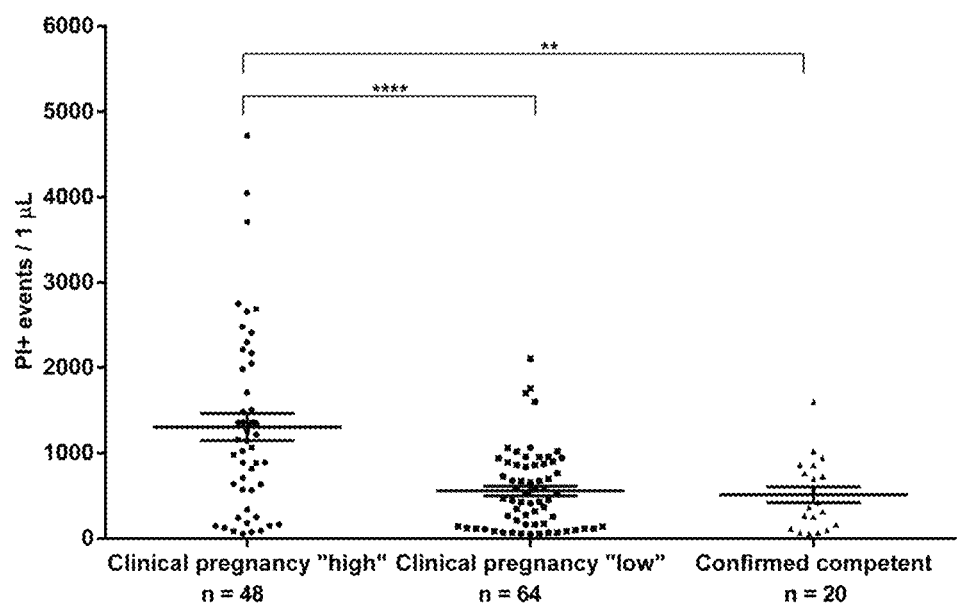

FIG. 7 Culture media of embryos from clinical pregnancies with higher (N=48) or lower (N=64) number of PI+EVs.*p<0.001, **p<0.0001

Figure 8A:
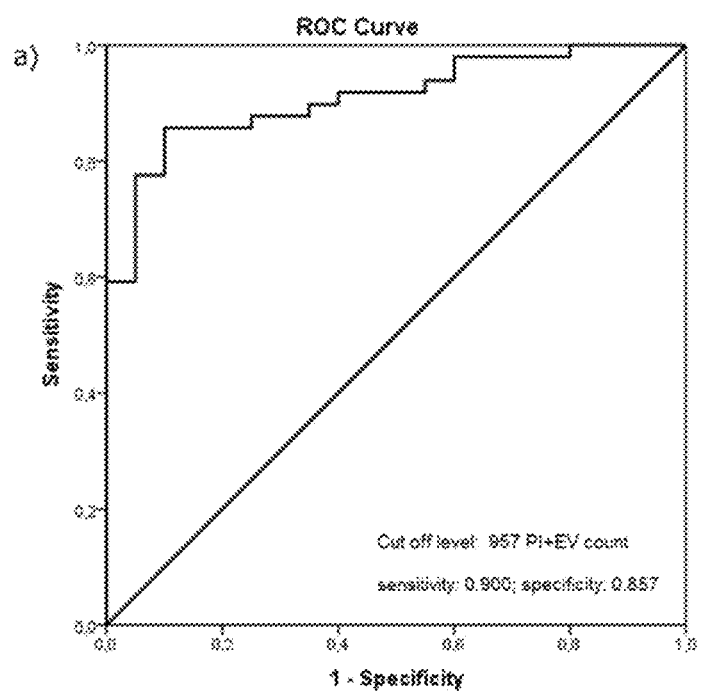
Figure 8B:
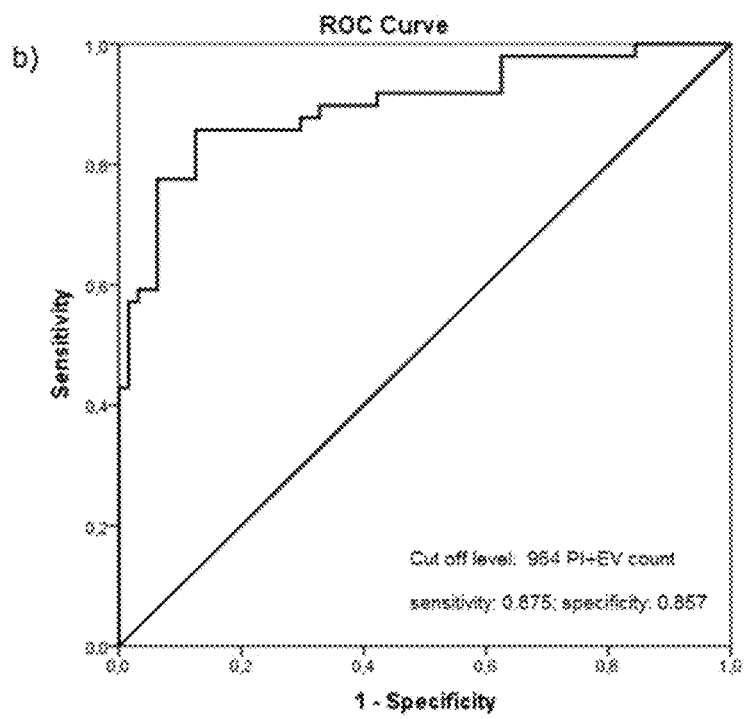

FIG. 8 Evaluation of optimal cut-off score and the diagnostic ability of test by ROC analysis
a) Data of confirmed competent embryos are plotted in function of data from implantation failure.
b) Data from presumed competent embryos (giving the lowest PI+EV values among embryos from the same mother) are plotted against data from implantation failure.
c) Data from presumed competent embryos are plotted against data from presumed incompetent embryos in the clinical pregnancy group, plus data from the implantation failure group.

Figure 9:
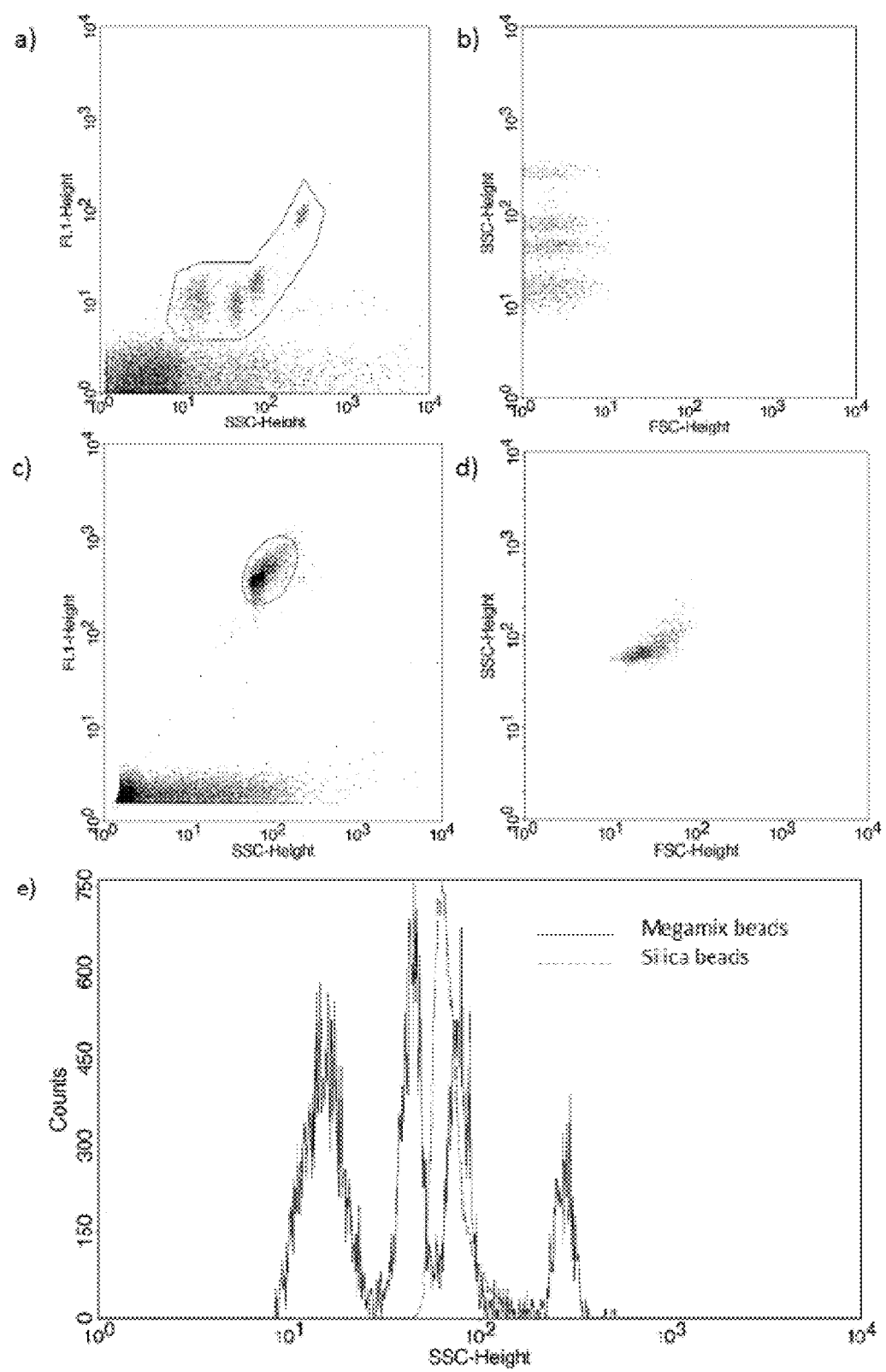
Figures 10A, 10B, 10C, 10D:
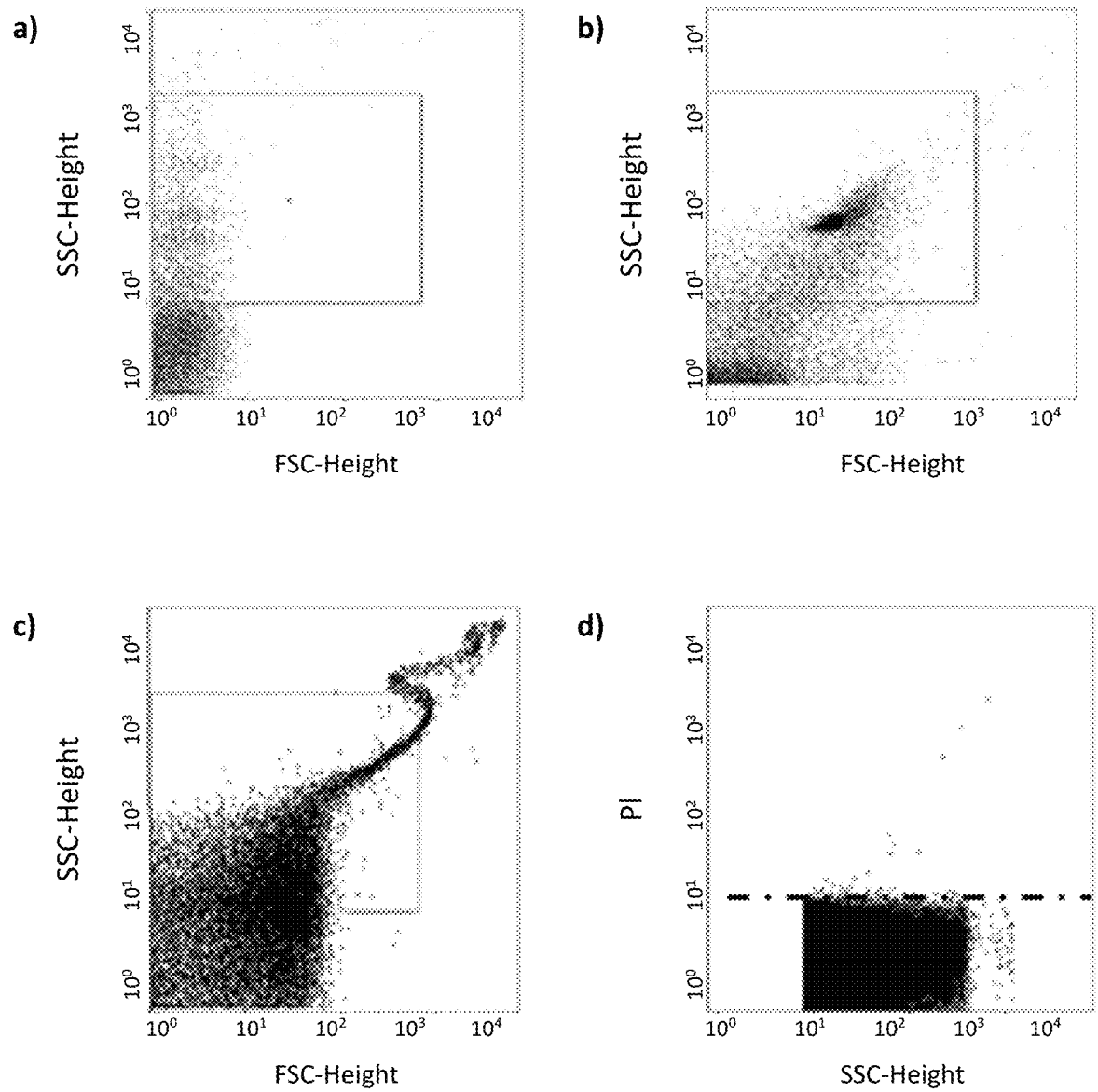
Figure 10E:
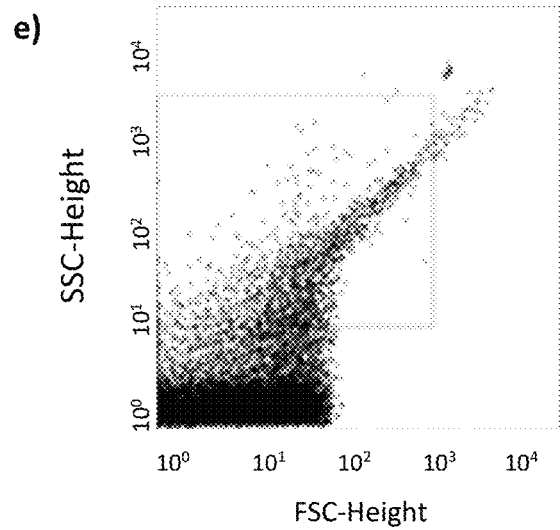
Figure 10F:
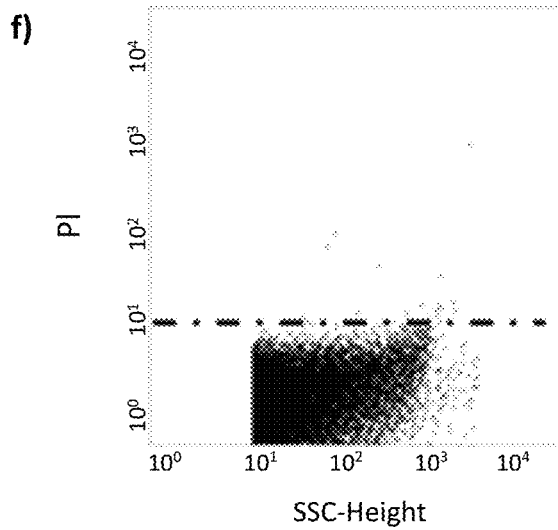
Figure 10G:
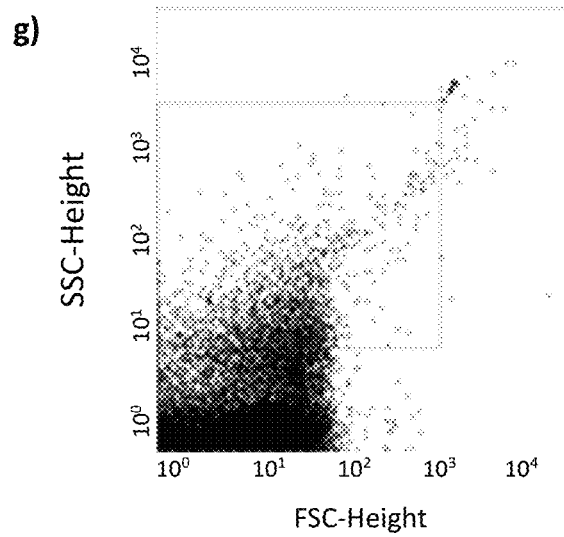
Figure 10H:
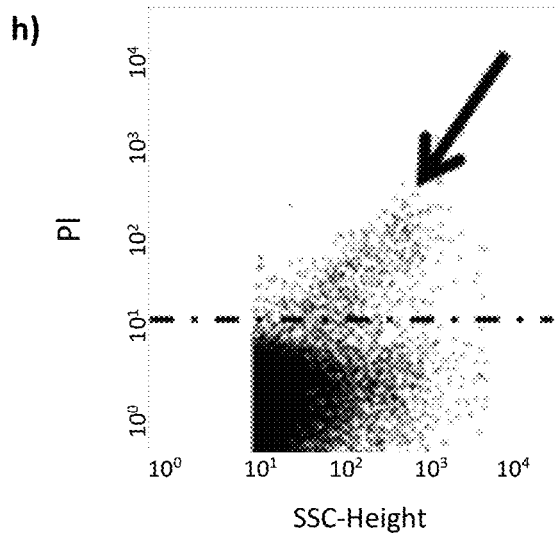

FIG. 9 Flow cytometer setup

Fluorescent Megamix-Plus SSC polystyrene beads (Biocytex, France) and Silica Beads Fluo-Green (Kisker Biotech GmbH & Co; Steinfurt, Germany) were used for optimization of cytometer settings. Although scatter parameters are determined by the morphology, size, absorption and refractive index of particles, these are also depending on laser characteristics. In the case of extracellular vesicles both scatter parameters (FSC, SSC) are primarily related to vesicle diameter. FACSCalibur (BD biosciences, USA) cytometers use photomultiplier tubes for the detection of SSC signals and photodiodes for FSC detection. It means that SSC parameter is more sensitive in FACSCalibur, so it can be used for extracellular vesicles. Comparative dot plots of SSC on X-axis vs. FL1 fluorescence on Y-axis show the fluorescence intensities of megamix (a) or silica (c) calibration beads. Dot plots of FSC on X-axis vs. SSC on Y-axis show the size distribution of megamix (b) or silica (d) calibration beads. Representative overlay histogram (e) compares the SSC parameters of megamix and silica beads. Peaks of solid curve represent the relative size of megamix bead populations (160 nm, 200 nm, 240 nm, 500 nm).

FIG. 10 EV population was defined by gating on FSC-SSC dot plot. Gating strategy based on FSC-SSC dot plots of Megamix-Plus SSC polystyrene beads (Biocytex, France) (a) and Silica Beads Fluo-Green (Kisker Biotech GmbH & Co; Steinfurt, Germany) (b). DNA staining was performed after paraformaldehyde fixation, so we could not apply differential detergent lysis for verifying the vesicles. In order to prove the staining specificity we calculated the fluorescence background noise. Propidium iodide (PI) stained embryo culture oil and unconditioned embryo culture medium was analysed by flow cytometry using the same instrument settings then in the case of IVF sample measurements. Dot plots of FSC on X-axis vs. SSC on Y-axis show the particle size distribution of embryo culture oil (c) or unconditioned embryo culture medium (e). Comparative dot plots of SSC on X-axis vs. FL2 fluorescence on Y-axis show the PI fluorescence background of embryo culture oil (d) or unconditioned embryo culture medium (f). g) and h) dot plots represent the size distribution (FSC vs. SSC) and the PI fluorescence (SSC vs. FL2) of conditioned embryo culture medium. Black arrow on h) dot plot indicates the PI+MVs.

Figure 11:
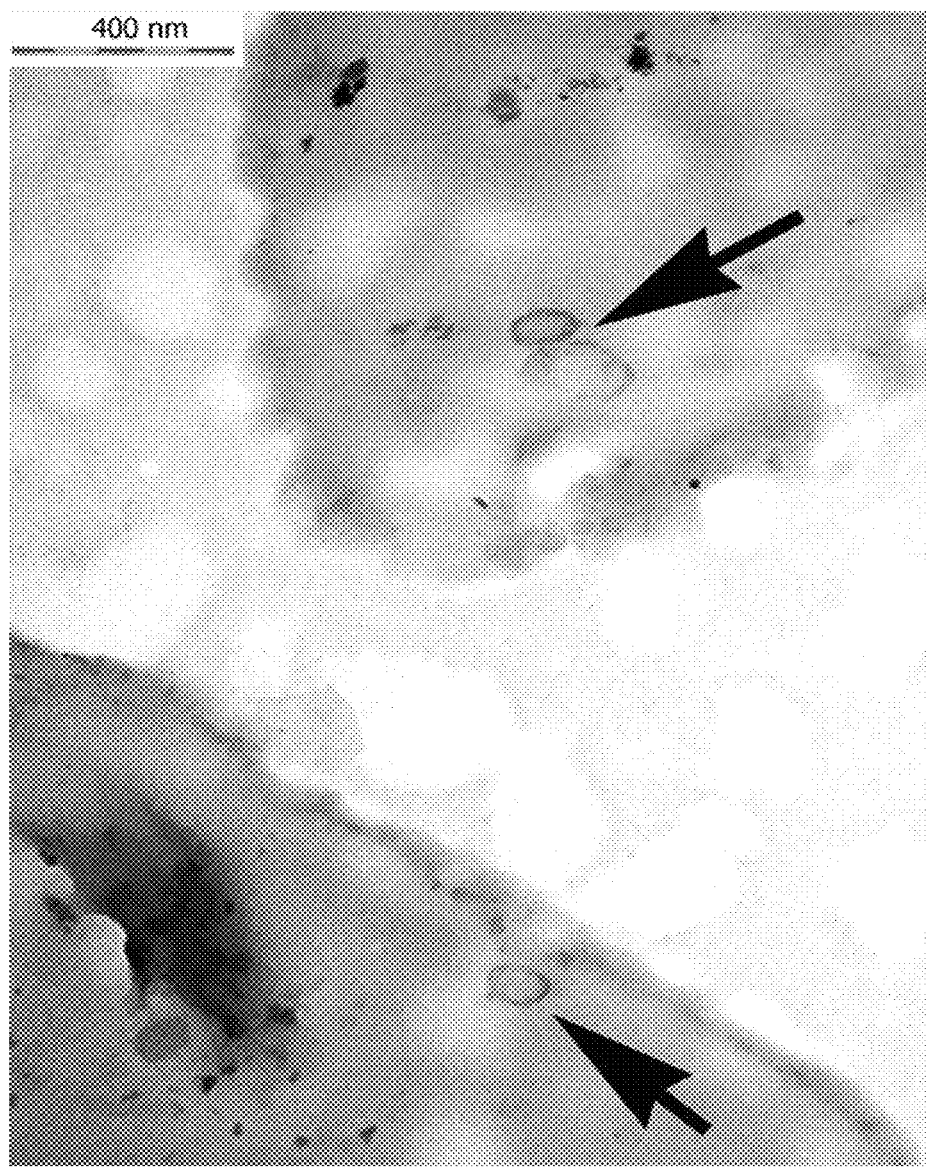

FIG. 11 Transmission electron microscope image of embryo derived EVs in IVF culture. The arrows indicate extracellular vesicles of 100 to 200 nm in culture medium of embryos. Four embryo culture media (40 μl each) were pooled, centrifuged at 12500 g for 20 min. The pellets were embedded for electron microscopy.

DETAILED DESCRIPTION OF THE INVENTION

The present inventors have found that in vitro fertilized cultured embryos release detectable numbers of EVs, into the culture media and a part of these contain nucleic acid detectable by PI staining. Furthermore, it has been demonstrated that in the cases of multiple transfer and singleton successful pregnancy, the culture medium of the embryo not resulting in clinical pregnancy contained higher amounts of nucleic acid-containing EVs than the culture medium or media of the embryo or embryos resulting in clinical pregnancy.

A non-invasive, simple, inexpensive, and most importantly quick test has been developed, to identify the embryos that are most likely to implant in a receptive endometrium. Less than 1 h is required to test 15 embryo culture media, thus the test can easily performed before fresh transfer.

Although the fact that in women with failed implantation the reason for the failure could be either embryonic, or maternal or both, must always be considered, the method of the invention is suitable to improve the prediction of clinical pregnancies. The method of the invention may be combined with other embryo viability assessment methods to further improve the reliability of the test outcome.

First, the presence of EVs in culture media of in vitro fertilized human embryos was demonstrated by AnnexinV binding to exofacial phosphatidylserine (PS) using FACS. Annexins are a family of calcium-dependent phospholipid-binding proteins that preferentially bind PS. Although PS is predominantly located in the inner leaflet of the plasma membrane, it is externalized in EVs. Phycoerythrin conjugated Annexin was used to make the detection of EVs possible by FACS. Although fetal calf serum containing unconditioned media also contained EVs, their number was lower, than in embryo culture media. Different types of culture media were found to contain different amounts of EVs. In the experiments described herein human embryos were cultured in media supplemented with human serum albumin, which did not contain PI+extracellular vesicles. To confirm the presence of EVs, Triton-X differential detergent lysis was used. Only events sensitive to Triton-X 100 lysis were considered as vesicles (FIG. 1). The presence of EVs was confirmed with transmission electron microscopy (FIG. 11). The number of EVs can be determined by adding counting beads to the sample. The same type of calibration beads are to be used in order to avoid inter-assay variations.

The above method is only suitable to detect EVs. To label nucleic acid inside a vesicle and to be able to detect the label by flow cytometry, the samples had to be fixed. After permeabilizing the membrane of the vesicle by fixing the sample with 4% formaldehyde, a fluorescent intercalating dye, propidium iodide has been used to stain the nucleic acid content of EVs (FIG. 2). To further confirm the presence of EVs, PI+EV containing media were subjected to TritonX treatment, upon which, the EVs disappeared. The number of PI+EVs was significantly (p<0.001) higher in the culture media of embryos that failed to implant (N=30 women, N=49 embryo culture media), than in those transferred to women with clinical pregnancy (N=58 women, N=112 embryo culture media) (FIG. 3) In the experiences described herein, PI was used as nucleic acid Identifying Embryos Having Limited Competence by Determining the Number of PI+EVs in the Culture Medium Transfer of 112 embryos to 58 women resulted in 64 implantations. Two embryos were transferred to 45 women, three to 5 women and a single embryo to 8 women. (One sample was used for other purposes, not included in the statistics). In 30 women the transfer of 49 embryos resulted in implantation failure.

If transfer of two embryos resulted in a singleton pregnancy, the culture media from one of the transferred embryos contained considerably less PI+EVs than the other (FIG. 4), while, if transfer of two embryos resulted in implantation failure, culture media of both embryos contained a high number of PI+EVs (FIG. 5).

In six cases transfer of two embryos resulted in twin pregnancy. The culture media of both embryos contained a low number of PI+EVs (FIG. 6). Accordingly, the embryos developing from the same female releasing higher number of PI+EVs were the ones that did not implant.

When transfer of more embryos resulted in singleton pregnancies, PI+EV counts were lower in one of the embryo culture media than in the others.

To prove this concept, culture media of embryos with a known outcome of the transfers were collected. Culture media from twenty embryos from either single transfers resulting in clinical pregnancies, or from transfer of two embryos resulting in twin pregnancies were tested.

When culture media with lower number of PI+EVs were analysed against culture media of embryos with higher number of PI+EVs within the "clinical pregnancy" group, there was a significant difference (p<0.001) between the lower PI+EV and higher PI+EV groups (FIG. 7). In 8 cases, transfer of a single embryo resulted in a singleton pregnancy, and in 6 cases, the transfer of two embryos ended up in a twin pregnancy. Nineteen out of these 20 "confirmed competent" embryos contained lower than the cut off level PI+EV counts (FIG. 7). This confirms, that the embryos having limited competence can indeed be identified by higher PI+EV counts.

Accordingly, if there is a marked difference in the PI+EV counts in the culture media of different embryos from the same mother, it is the embryo with higher number of nucleic acid-containing EVs that is less likely to implant. Table 1 shows the number of nucleic acid-containing EVs in the tested culture media.

TABLE 1

| Female ID number | Number of nucleic acid-containing Evs in culture medium of the embryo | | | | |
|---|---|---|---|---|---|
| | implantation | implantation | failure | failure | failure |
| 1 | 956 | | 2297 | | |
| 2 | 938 | | 2405 | 1354 | |
| 3 | 276 | | 1981 | | |
| 4 | 673 | | 1710 | | |
| 5 | 163 | | 4719 | | |
| 6 | 86 | | | | |
| 7 | 141 | | 165 | | |
| 8 | 121 | | 180 | | |
| 9 | 164 | 115 | | | |
| 10 | 116 | | 248 | | |
| 11 | 899 | | 1481 | | |
| 12 | 838 | | 1065 | | |
| 13 | 345 | | 2168 | | |
| 14 | 575 | | 1143 | | |
| 15 | 451 | | 712 | | |

TABLE 1-continued

| Female ID number | Number of nucleic acid-containing Evs in culture medium of the embryo | | | | |
|---|---|---|---|---|---|
| | implantation | implantation | failure | failure | failure |
| *16* | 1058 | | 1355 | | |
| *17* | 2104 | | 4051 | | |
| *18* | | | 2657 | 2477 | |
| *19* | 1757 | | 2044 | 3711 | |
| *20* | 1702 | | 2688 | | |
| *21* | 1600 | | | | |
| *22* | | | 890 | | |
| *23* | 213 | | | | |
| *24* | | | 151 | | |
| *25* | | 70 | | | |
| *26* | 70 | | 126 | | |
| *27* | 60 | | 94 | | |
| *28* | | | 56 | | |
| *29* | 54 | | 75 | | |
| *30* | 70 | 56 | | | |
| *31* | 98 | | | | |
| *32* | 66 | | 87 | | |
| *33* | 254 | 174 | 246 | | |
| *34* | 86 | | 148 | | |
| *35* | 116 | 111 | | | |
| *36* | 143 | | 340 | | |
| *37* | 266 | 319 | | | |
| *38* | 425 | | | | |
| *39* | 366 | 861 | | | |
| *40* | 467 | | 573 | | |
| *41* | 678 | | 1024 | | |
| *42* | 659 | | 889 | | |
| *43* | 428 | 531 | 886 | | |
| *44* | 518 | | 636 | | |
| *45* | 586 | | | | |
| *46* | 443 | | 570 | | |
| *47* | 675 | | 818 | | |
| *48* | 874 | | 1360 | | |
| *49* | 859 | | | | |
| *50* | 952 | | 980 | | |
| *51* | 1022 | 764 | | | |
| *52* | 1019 | | 2753 | 1360 | |
| *53* | 697 | | | | |
| *54* | 589 | | 2211 | | |
| *55* | 414 | | 636 | | |
| *56* | 890 | | 1215 | | |
| *57* | 1061 | | 1502 | | |
| *58* | 943 | 725 | | | |
| *59* | | | 2082 | | |
| *60* | 310 | | 1425 | | |
| *61* | | | 340 | | |
| *62* | | | 1357 | 1802 | 1531 |
| *63* | | | 1113 | 1362 | |
| *64* | 280 | | 805 | | |
| *65* | | | 2183 | | |
| *66* | | | 988 | | |
| *67* | | | 2147 | | |
| *68* | 972 | | 3620 | | |
| *69* | 1015 | | 2823 | | |
| *70* | | | 1241 | | |
| *71* | | | 1018 | 1263 | |
| *72* | | | 1436 | | |
| *73* | 1516 | | 3081 | | |
| *74* | | | 2454 | | |
| *75* | | | 1720 | 1966 | |
| *76* | | | 2570 | 2990 | |
| *77* | | | 5501 | | |
| *78* | | | 4261 | | |
| *79* | | | 5487 | 7132 | |
| *80* | | | 1803 | | |
| *81* | | | 5117 | 4904 | |
| *82* | | | 6962 | 720 | |
| *83* | | | 1799 | 597 | |
| *84* | | | 2753 | | |
| *85* | | | 1876 | 2365 | |
| *86* | | | 2931 | | |
| *87* | | | 4575 | | |
| *88* | | | 2908 | 2203 | |

Female ID NO in italics: "implantation" group,
bold numbers: "confirmed competent"

A Cut Off Level for Identifying Embryos Having Limited Competence.

In order to identify embryos that are less likely to result in a clinical pregnancy, ROC (receiver operating characteristic) analysis was performed using different data sets. Optimal cut-off score was set by the Youden index. It is self evident that any suitable statistical method may be used to determine optimal cut-off score.

Plotting data of confirmed competent embryos versus data from implantation failure (FIG. 8a) yielded a cut off level of 957 PI+EV count that corresponded to a maximum specificity and sensitivity. The AUC (area under the curve) was 0.91, (95% CI: 0.842-0.978). Sensitivity; 0.9 specificity; 0.857

Plotting data from presumed competent embryos (giving the lowest PI+EV values among embryos from the same mother) against data from implantation failure (FIG. 8b) resulted in a cut off level of 964. The AUC was 0.899 (95% CI: 0.837-0.960) Sensitivity; 0.875 specificity; 0.857

Figure 8C:
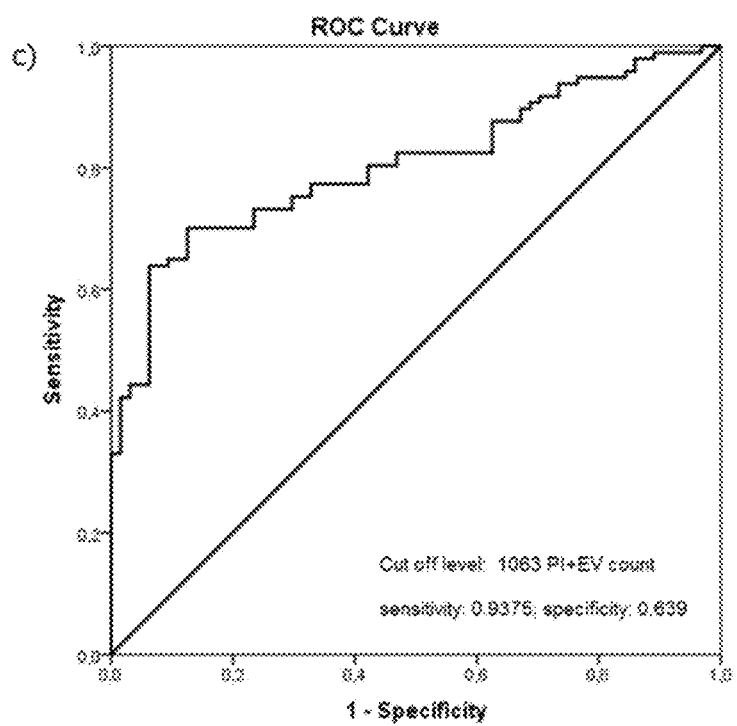

Plotting data from presumed competent embryos against data from presumed incompetent embryos in the clinical pregnancy group, plus data from the implantation failure group (FIG. 8c). The cut off value was 1063, the AUC was 0.806 (95% CI: 0.740-0.873) Sensitivity; 0.9375 specificity; 0.639

The AUC is a measure of how well a parameter can distinguish between two diagnostic groups. The present values show a very good distinction.

When the cut off was set at 964 PI+EVs, the culture media of 8 (12.5%) out of 64 potentially competent embryos contained a higher number of PI+EVs than the cut off, whereas in 7 (14%) of the 49 samples from the implantation failure group PI+EV counts fell below the cut off level. The culture media of 19 out of the 20 "confirmed competent" embryos contained lower PI+EV counts than the cut off level.

Considering the relatively small sample size, the sensitivity and specificity of the test are acceptable.

A possible method to determine a cut off level for identifying embryos with limited competence comprises the following steps:
  determining the number of nucleic acid-containing extracellular vesicles in samples of a plurality of culture medium of the same type which were used to culture the embryos,
  relating the number of nucleic acid-containing extracellular vesicles in said samples to the outcome of the transfer,
  determining the number of nucleic acid-containing extracellular vesicles that distinguishes the culture media from embryos that implanted from those that did not.ROC analysis provides a reliable and accepted method to determine the number of nucleic acid-containing extracellular vesicles that distinguishes the culture media from embryos that implanted from those that did not, i.e. cut off values. More information is found on ROC analysis e.g. in Metz[22], Zhou[23], Karimollah[24], and on the Youden index in e.g. Youden[25], Ruopp et al.[26].

Timing of the Assessment of Embryo Competence

The method for non-invasive embryo competence assessment may be performed at any time before transferring the embryo provided that nucleic acid-containing EVs are detectable in the sample. Embryo culture media are conventionally sampled 3 or 5 days after the oocyte fertilization (oocyte, retrieval, start of culturing). Preferably, method for non-invasive embryo competence assessment is performed on day 5, right before transfer.

The advantage of day 5 transfer is that if the embryo is cultured in vitro till it develops into blastocyst, the developmental uncertainties of cleavage stage embryo development can be eliminated. Furthermore, the implantation potential of the blastocyst seems to be better than that of cleavage stage embryos. A single-blastocyst transfer is much more likely to result in a singleton live birth, than transfer of a single good-quality cleavage-stage embryo on day 3[12,36]. Therefore, simply allowing the embryo to reach the blastocyst stage, might improve the implantation rate in a fresh transfer.

Culture Medium

Any culture medium suitable for culturing a human embryo might be used in the method according to the invention. It has been found that differently supplemented culture media contained different amounts of extracellular vesicle, e.g. culture medium supplemented with fetal calf serum contained more EVs than culture medium supplemented with human serum albumin. None of the tested culture media contained PI+EVs.

Embryo-derived nucleic acid positive (PI+) EVs may be detected in any culture medium suitable for embryo culture. For each type of culture medium the comparison between empty and spent medium may be performed. Detection and determination of the number of EVs in the embryo culture medium may be performed by e.g. electronmicroscopy or flow cytometry.

When determination of the number of EVs in the culture medium is performed using flow cytometry, the method may comprise the following steps:
providing a sample of the culture medium,
staining EVs in the sample by a dye suitable for staining Evs,
applying differential detergent lysis on the sample,
identifying events that are sensitive to differential detergent lysis as EVs.

EVs may be stained by fluorochromes suitable for flow cytometry that stain vesicle membrane, or antibodies suitable for flow cytometry that target specific cell-of-origin antigens. Flurochromes and antibodies suitable for flow cytometry are e.g. fluorescent lipophilic dyes or antibodies. Cationic lipophilic dyes which may be used to stain vesicle membrane are e.g. CMXRos, JC-1, $DiOC_6$, rhodamine. Annexins are a family of calcium-dependent phospholipid-binding proteins that preferentially bind phosphatidylserine (PS), which is externalized during EV production. In a preferred embodiment, fluorochrome labelled annexins are used for the staining of EVs.

Commercially available detergents may be used for differential detergent lysis. For example, Triton X-100, polysorbate 20, polysorbate 40, polysorbate 60, polysorbate 80, sodium dodecyl sulfate, and Igepal-CA630 are suitable detergents. Triton X-100 is a preferred detergent for the lysis of EVs.

The absolute number of EVs can be determined by adding counting beads—as an internal standard—to the sample.

Flow Cytometry

Microbead-based assessments were applied for FACSCalibur cytometer. In these cases the appropriate sample handling is very important to avoid false results or artefacts. The data indicate that during microbead-based absolute counting procedures the same type of calibration beads should be used in order to avoid inter-assay variations. In order to achieve the highest sensitivity the detection of background noise by the analysis of nucleic acid stain (PI) containing empty culture media is also suggested (FIGS. 9 and 10).

It is to be understood that different instruments use different counting methods. Volumetric-based absolute counting may also be used in the method according to the invention.

Nucleic Acid Stain

Nucleic acid in the EVs has been stained by propidium iodide in the experiments described herein. It is to be noted however, that other nucleic acid dyes may be used in the method of the invention, which may be less or more specific for DNA over RNA.

EXAMPLES

Methods

Patients, Sample Collection

Eighty eight unselected infertile patients, enrolled in the IVF program, were included in the study. The study was approved by the Human Reproduction Committee of the Hungarian Medical Research Council and the Ethical Committee of Pecs University. Informed consent was obtained from each patient. All methods were performed in accordance with the relevant guidelines and regulations.

For controlled ovarian hyperstimulation follicles were sycnhronized with the GnRh agonist triptorelin (Gonapeptyl; Ferring®, Germany) in either a long or short protocol. Follicle stimulation was performed with individual dosages of rFSH (Gonal-F; Serono® Aubonne, Switzerland), varying from 112 to 225 IU per day. Final oocyte maturation was induced by injection of 250 μg of hCG (Ovitrelle; Serono® Aubonne, Switzerland). Oocytes were harvested 36 hours later by ultrasonographically guided puncture of the follicles. Fertilization was performed with intracytoplasmatic sperm injection (ICSI) if sperm count was less than 15 M/ml, or the maternal age was higher than 35 years or if the number of the previous treatment cycles of the patient were more than two.

Embryos were cultured individually for 3 days under oil in G-1 medium. Then the medium was replaced by 40 μl of G-2 medium and the embryos were further cultured under oil till day 5. In the morning of day 5 (the day of the transfer) as much as possible of the spent medium was collected, and stored at −80° C. until used for EV determination. Oil (Ovoil), G-1 and G-2 medium were purchased from Vitrolife®, Goteborg, Sweden.

Embryos were transferred 3 or 5 days after the oocyte retrieval, however, only day 5 media from embryos transferred on day 5 were included in this study. The embryos to be transferred were selected by morphological criteria, using the Istambul Consensus embryo scoring system of ESHRE32. If possible, only expanded blastocysts with Grade 1 ICM and IL were transferred.

Implantation was confirmed by ultrasonography four weeks after the transfer. Clinical pregnancy is defined by the presence of foetal heartbeat, and implantation failure by the lack of the former, together with the lack of beta hCG on week 2 after the transfer.

Two groups were formed according to the outcome;
1) Implantation failure N=30
2) clinical pregnancy N=58

The number of PI+EVs was significantly (p<0.001) lower in the 5th day culture media of embryos from the "clinical pregnancy" group (N=112), than in those of embryos, that failed to implant (N=49) (FIG. 3)

Flow Cytometry

Measurements were carried out using a BD FACSCalibur (BD Biosciences) flow cytometer. All the FACS data were analyzed with CellQuestPro software. The instrument settings and gates were defined by Megamix-Plus SSC beads (Biocytex, France) and were optimized with 1 µm Silica Beads Fluo-Green Green (Kicker Biotech GmbH & Co; Steinfurt, Germany). (FIG. 1.) The single-platform flow cytometric determination of the absolute number of EVs was performed by adding internal counting standard beads (Sysmex Partec GmbH; Germany) to IVF conditioned medium samples. The absolute number of EVs was calculated using the following formula:

$$\text{Absolute } EV \text{ Count}(EVs/\mu L) = (\text{Number of } EV \text{ events}/\text{Number of bead events}) \times \text{Concentration of beads (beads}/\mu L)$$

For Annexin V staining 2 µl IVF conditioned medium was diluted with 250 µl annexin binding buffer (BD Biosciences, San Jose, USA) and incubated for 10 minutes at room temperature with 1 µl phycoerythrin conjugated AnnexinV (BD Biosciences, San Jose, USA). Fifty µl Count Check Beads (Sysmex Partec GmbH) was also added for determination of the number of EVs. To confirm the presence of EVs, we applied Triton-X differential detergent lysis using a final concentration of 0.1%. Only events that disappeared in the presence of 0.1% Triton-X 100 were considered as vesicles[20,21].

Propidium iodide (PI) was used for the labelling of the nucleic acid content of embryo-derived EVs. PI is a fluorescent intercalating agent which is commonly used as a DNA stain for flow cytometry. Although PI may bind both DNA and RNA, it is most often used to quantitatively assess DNA content. Therefore it is presumed that the PI+EVs contain DNA. 25 µl of conditioned embryo culture media was used for the measurements. Embryo culture media were incubated for 15 minutes at room temperature with 100 µl 4% formaldehyde (from paraformaldehyde (PFA) solution. At the end of the incubation, 150 µl filtered PBS and 1 µl PI solution (50 µg/ml) and 50 µl Count Check beads (Sysmex Partec GmbH) were added to the sample. FACS analysis was carried out within 30 minutes after PI staining. Unstained samples were used for the detection of autofluorescence. Empty G-1 and G-2 medium and oil for embryo culture were also incubated together PI dye for determination of the specificity of DNA labelling method. (FIG. 10). The single-platform flow cytometric determination of the absolute number of EVs was performed by adding internal counting standard beads (Sysmex Partec GmbH; Germany) to IVF conditioned medium samples.

Confirmation of the Presence of EVs in IVF Medium by Using Transmission Electron Microscopy Pooled samples (2 IVF medium) were used for transmission electron microscopic analysis. After centrifugation of pooled samples (20500 g, 20 minutes), the supernatant was carefully removed and the pellet was fixed at room temperature for 30 min with 4% formaldehyde, in 0.01 M phoshate buffer (PBS) at pH 7.4). After washing with phosphate buffer several times, the preparations were post-fixed in 1% OsO4 (Taab; Aldermaston, Berks, UK) for 30 min. Following washing with distilled water, the pellets were dehydrated in graded ethanol, including block-staining with 2% uranyl acetate in 70% ethanol for 30 min, and embedded in Taab 812 (Taab). Ultrathin sections were examined in a Hitachi 7100 transmission electron microscope (Hitachi Corporation, Japan). Electron micrographs were taken at the same magnification (40,000).

Statistical Analysis

The distribution of the PI positive (PI+) EVs was tested with the Kolgomorov-Smirnov's test, which showed a non-parametric distribution. To determine differences between the groups the Mann-Whitney test was used. Receiver operating curve (ROC) analyses was used evaluate the diagnostic ability of test, and the optimal cut-off score was set by the Youden index35. P-values<0.05 were considered as statistically significant.

Results of the Cut-Off Value Analysis

Based on the data presented herein, the embryo not to be transferred should be the one with the highest PI+EV count among all the embryos from the same mother. The question is, how many of such embryos have a lower PI+EV count, than the cut-off level, in other words; what is the chance for false positivity. In the present study, 8 (12.5%) of the 64 supposedly competent embryos were falsely diagnosed. Therefore, when an IVF specialist transfers the embryo with the lowest PI+EV count, the chances of implantation are close to 90%, provided the maternal side is receptive.

REFERENCES

1. Munne S, Alikani M, Tomkin G, Grifo J, Cohen J: Embryo morphology, developmental rates and maternal age are correlated with chromosome abnormalities. Fertil Steril 1995; 64: 382-391.
2. Magli M C, Gianaroli L, Ferrareti A P: Chromosomal abnormalities in embryos. Mol Cell Endocrinol 2001; 183 (suppl. 1): S29-S34.
3. Márquez C, Sandalinas M, Bahçe M, Alikani M, Munne S: Chromosome abnormalities in 1255 cleavage-stage human embryos. Reprod BioMed Online 2000; 1: 17-26.
4. Bielanska M, Tan S L, Ao A: High rate of mixoploidy among human blastocysts cultured in vitro. Fertil Steril 2002; 78: 1248-53.
5. Rai R, Regan L: Recurrent miscarriage. Lancet 2006; 368: 601-611.
6. Mertzanidou A, Wilton L, Cheng J, Spits C, Vanneste E, Moreau Y, Vermeesch J R, Sermon K: Microarray analysis reveals abnormal chromosomal complements in over 70% of 14 normally developing human embryos. Hum Reprod 2013; 28: 256-264.
7. Vanneste, E, Voet T, Le Caignec C, Ampe M, Konings P, Melotte C, Debrock S, Amyere M, Vikkula M, Schuit F, Fryns J P, Verbeke G, D'Hooghe T, Moreau Y, Vermeesch J R.: Chromosome instability is common in human cleavage-stage embryos. Nat Med 2009; 15: 577-583.
8. Quenby S, Vince G, Farquharson R, Aplin J: Recurrent miscarriage: a defect in nature's quality control? Hum Reprod 2002; 17:1959-1963.
9. Stephenson M D, Awartani K A, Robinson W P: Cytogenetic analysis of miscarriages from couples with recurrent miscarriage: a case-control study. Hum Reprod 2002; 17:446-451.

10. Macklon N S, Geraedts J P, Fauser B C: Conception to ongoing pregnancy: the 'black box' of early pregnancy loss. Hum Reprod Update 2002; 8:333-343.
11. Yáñez-Mó M, Siljander P R, Andreu Z, Zavec A B, Borràs F E, Buzas E I, Buzas K, Casal E, Cappello F, Carvalho J, Colás E, Cordeiro-da Silva A, Fais S, Falcon-Perez J M, Ghobrial I M, Giebel B, Gimona M, Graner M, Gursel I, Gursel M, Heegaard N H, Hendrix A, Kierulf P, Kokubun K, Kosanovic M, Kralj-Iglic V, Krämer-Albers E M, Laitinen S, Lässer C, Lener T, Ligeti E, Linē A, Lipps G, Llorente A, Lötvall J, Manček-Keber M, Marcilla A, Mittelbrunn M, Nazarenko I, Nolte-'t Hoen E N, Nyman T A, O'Driscoll L, Olivan M, Oliveira C, Pállinger É, Del Portillo H A, Reventós J, Rigau M, Rohde E, Sammar M, Sánchez-Madrid F, Santarém N, Schallmoser K, Ostenfeld M S, Stoorvogel W, Stukelj R, Van der Grein S G, Vasconcelos M H, Wauben M H, De Wever O. Biological properties of extracellular vesicles and their physiological functions. J Extracell Vesicles. 2015 May 14; 4:27066. doi: 10.3402/jev.v4.27066. eCollection 2015.
12. György B, Szabó T G, Pásztói M, Pál Z, Misják P, Aradi B, László V, Pallinger E, Pap E, Kittel A, Nagy G, Falus A, Buzás E I. Membrane vesicles, current state-of-the-art: emerging role of extracellular vesicles. Cell Mol Life Sci. 2011 August; 68(16):2667-88. Epub 2011 May 11.
13. Dionne Tannetta, Rebecca Dragovic, Zahraa Alyahyaei and Jennifer Southcombe Extracellular vesicles and reproduction-promotion of successful pregnancy. Cellular & Molecular Immunology (2014) 11, 548-563
14. Jin Cai, Yu Han, Hongmei Ren, Caiyu Chen, Duofen He, Lin Zhou, Gilbert M. Eisner, Laureano D. Asico, Pedro A. Jose, and Chunyu Zeng Extracellular vesicle-mediated transfer of donor genomic DNA to recipient cells is a novel mechanism for genetic influence between cells. Journal of Molecular Cell Biology (2013), 5, 227-238
15. Jenna Kropp, Sana M. Salih and Hasan Khatib Expression of microRNAs in bovine and human pre-implantation embryo culture media. Frontiers in Genetics April 2014 Volume 5 Article 91
16. Mincheva-Nilsson L: Placental exosome-mediated immune protection of the fetus: feeling groovy in a cloud of exosomes. Expert Rev Obstetrics Gynaecol 2010, 5:619-634.
17. Kshirsagar S, Alam S, Jasti S, Hodes H, Nauser T, Gilliam M, Billstrand C, Hunt J, Petroff M Immunomodulatory molecules are released from the first trimester and term placenta via exosomes. Placenta 2012, 33:982-990.
18. van der Pol E, Hoekstra A G, Sturk A, Otto C, van Leeuwen T G, Nieuwland R (2010). "Optical and non-optical methods for detection and characterization of microparticles and exosomes". J. Thromb. Haemost. 8 (12): 2596-607.
19. Y. J. Ferreira, C. Gardiner, M. Poli, K. Turner, T. Child, and I. L. Sargent Embryo quality: does it predict pregnancy? eshre Annual Meeting London, 7-10 Jul. 2013 Selected Oral Comminucations, Session 66, 10 Jul. 2013
20. György B, Módos K, Pállinger E, Pálóczi K, Pasztoi M, Misják P, Deli M A, Sipos A, Szalai A, Voszka I, Polgár A, Tóth K, Csete M, Nagy G, Gay S, Falus A, Kittel A, Buzás E I. Detection and isolation of cell-derived microparticles are compromised by protein complexes resulting from shared biophysical parameters. Blood. 2011 Jan. 27; 117(4):e39-48. Epub 2010 Nov. 1.
21. Osteikoetxea X, Sódar B, Németh A, Szabó-Taylor K, Pálóczi K, Vukman K V, Tamási V, Balogh A, Kittel Á, Paflinger É, Buzás E I. Differential detergent sensitivity of extracellular vesicle subpopulations. Org Biomol Chem. 2015 Sep. 23; 13(38):9775-82. doi: 10.1039/c5ob01451d.
22. Metz Basic Principles of ROC Analysis Seminars in Nuclear Medicine, Vol. VIII. No. 4, 1978
23. Zhou, Xiao-Hua; Obuchowski, Nancy A.; McClish, Donna K. (2002). Statistical Methods in Diagnostic Medicine. New York, N.Y.: Wiley & Sons. ISBN 978-0-471-34772-9.
24. Karimollah Hajian-Tilaki Receiver Operating Characteristic (ROC) Curve Analysis for Medical Diagnostic Test Evaluation Caspian J Intern Med 2013; 4(2): 627-635
25. Youden, W. J. An index for rating diagnostic tests Cancer, 3, 32-35, (1950)
26. Ruopp et al. Youden Index and Optimal Cut-Point Estimated from Observations Affected by a Lower Limit of Detection Biom J. 2008 June; 50(3): 419-430

The invention claimed is:

1. A method for improving probability of development of clinical pregnancy, said method comprising the following steps:
   a) individually culturing embryos developed from in vitro fertilized oocytes derived from one female in a plurality of culture media of the same type,
   b) measuring the number of nucleic acid-containing extracellular vesicles (EV) in samples of each of the plurality of culture media of the same type, which were used to culture the embryos,
   c) identifying one of the embryos with a lower number of nucleic acid-containing EVs in its culture medium relative to another one of the embryos with a higher number of nucleic acid-containing EVs in its culture medium and
   d) transferring the embryo having a lower number of nucleic acid-containing EVs in its culture medium into the female.

2. The method according to claim 1, wherein the nucleic acid is DNA.

3. The method according to claim 1, wherein step b) comprises
   i) fixing the samples,
   ii) staining the EVs in the samples by a fluorescent nucleic acid stain suitable for use in flow cytometry, iii) analysing the EVs stained by the nucleic acid stain using flow cytometry.

4. The method according to claim 3, wherein the nucleic acid stain is a DNA stain.

5. The method according to claim 3, wherein the samples are fixed with formaldehyde or paraformaldehyde.

6. The method according to claim 3, wherein the fluorescent stain suitable for use in flow cytometry is propidium iodide or a cyanine dye.

7. The method of claim 1, wherein steps b) and c) of the method are performed immediately before embryo transfer to the female.

8. The method of claim 1, wherein step b) of the method is performed on day 5 after in vitro fertilization.

9. The method of claim 1, wherein the competence of the transferred embryo is confirmed by confirming clinical pregnancy.

10. The method of claim 1 wherein the embryo having a higher number of nucleic acid-containing EVs in its culture medium is not transferred into the female.

11. The method of claim 1 wherein the embryo having a lower number of nucleic acid-containing EVs in its culture medium is the only one of the cultured embryos transferred into the female.

* * * * *